(12) United States Patent
Fukuta et al.

(10) Patent No.: US 6,187,340 B1
(45) Date of Patent: Feb. 13, 2001

(54) STABILIZED PHARMACEUTICAL PREPARATION

(75) Inventors: Makoto Fukuta, Nara; Hiroki Itoh, Suita, both of (JP)

(73) Assignee: Takeda Chemical Industries, Ltd., Osaka (JP)

( * ) Notice: Under 35 U.S.C. 154(b), the term of this patent shall be extended for 0 days.

(21) Appl. No.: 09/149,122

(22) Filed: Sep. 9, 1998

(30) Foreign Application Priority Data

Sep. 10, 1997 (JP) .................................................. 9-245778

(51) Int. Cl.$^7$ ........................................................ A61K 9/28
(52) U.S. Cl. .......................... 424/474; 424/475; 424/451; 424/463; 424/490; 424/464
(58) Field of Search .................... 424/474, 475, 424/490, 464, 451, 463

(56) References Cited

U.S. PATENT DOCUMENTS

| 4,636,261 | 1/1987 | Heinze ................................. 106/289 |
| 5,322,698 | * 6/1994 | Kovács et al. ........................ 424/480 |
| 5,593,691 | * 1/1997 | Eugster et al. ........................ 424/461 |

FOREIGN PATENT DOCUMENTS

| 0 277 741 A1 | 8/1988 | (EP) . |
| 1086150 | 11/1965 | (GB) . |
| 85/01207 | 3/1985 | (WO) . |

OTHER PUBLICATIONS

Database WPI, Section Ch, Week 810918, Dec. 1980, Derwent Publications Ltd., GB; AN 81–14309D XP002087481 & JP 55 162715 A (Takeda) * abstract *.

S. Basquin et al., "Development of the use of Canthaxanthin for Coloring Film Coated Tablets", Labo–Pharma—Probl. Tech., No. 334, Sep. 1983, pp. 632–637, XP002087480. (with translation).

D. Bindra et al., "Degradation of $O^6$–Benzylguanine in Aqueous Polyethylene Glycol 400 (PEG 400) Solutions: Concerns with Formaldehyde in PEG 400", Pharmaceutical Research, vol. 11, No. 7 pp. 1060–1064, (1994).

* cited by examiner

Primary Examiner—Michael A. Williamson
(74) Attorney, Agent, or Firm—Wenderoth, Lind & Ponack, L.L.P.

(57) ABSTRACT

A stabilized pharmaceutical preparation which is coated with a coating agent comprising an agent for the protection from light, said agent being capable of producing free radicals when exposed to ultraviolet rays, and a free radical scavenger; which is stable to light, especially ultraviolet rays, or heat, and which has excellent storage-stability.

19 Claims, No Drawings

STABILIZED PHARMACEUTICAL PREPARATION

BACKGROUND OF THE INVENTION

1. Technical Field

The present invention relates to a pharmaceutical preparation which is stable to light (especially ultraviolet rays) or heat, and which has excellent storage-stability; and a coating agent which is a raw material of such a pharmaceutical preparation.

2. Background Art

It has been found that $O^6$-benzylguanine is decomposed in an aqueous solution of polyethylene glycol 400 at room temperature by the reaction of formaldehyde (present as an impurity of polyethylene glycol 400 and probably produced by air oxidation of polyethylene glycol 400) with $O^6$-benzylguanine [Pharmaceutical Research, 11 (7), 1060–1064 pp. (1994)].

JP-A-63-301816 (EP-A1-0277741) mentions an enteric coating using an enteric film-liquid including titanium oxide and polyethylene glycol 6000.

Chemical Abstracts 122:388853 mentions tablets containing vitamin C, Yinqiao extracts, acetaminophen, chlorphenramine, calcium carbonate, starch, dextran, peppermint oil and Yinqiao and jingfang volatile oils coated with a composition containing hydroxypropylmethyl cellulose, no.2 enteric vinyl resin, PEG 6000, sesame oil, Tween 80, titanium oxide, talc, Mg stearate, food color, 95% ethanol, and distilled water.

JP-A-63-166824 mentions soft capsules comprising oily solution containing pharmaceutically active ingredient unstable in light, coated with a coating agent containing fine particles of titanium oxide of at least 85% with particle size of 0.1 µm or less.

When a pharmaceutical preparation which is unstable to light is provided to consumers, the pharmaceutical preparation has to be wrapped or coated for protection from light. However, when storage conditions of a pharmaceutical preparation at a pharmacy in a hospital or at patients are considered, it is difficult to say that sufficient quality of the pharmaceutical preparation is guaranteed by wrapping for protection from light. Therefore, when a pharmaceutical preparation which is unstable to light is manufactured, coating for protection from light is desired.

However, in case of manufacturing a pharmaceutical preparation comprising a drug which is unstable to light, when a tablet comprising the drug was coated with a coating agent which comprises an agent for protection from light such as titanium oxide and a plasticizer such as polyethylene glycol, there was a problem that the obtained film-coated tablet was less stable to light than before coating.

SUMMARY OF THE INVENTION

In view of such a problem, when the stability of a drug in a film-coated tablet was studied, it was found that 1) titanium oxide in a coating agent produces free radicals when exposed to ultraviolet rays, 2) free radicals decompose an alcohol such as polyethylene glycol, etc., in a coating agent, or a drug, 3) decomposition products of an alcohol such as polyethylene glycol in a coating agent, for instance, an aldehyde such as formaldehyde, acetaldehyde, etc., an acid such as formic acid, etc., or a peroxide, also decomposes a drug.

As a result of further studies to remove the factors making the drugs unstable and to obtain various stabilized pharmaceutical preparations based on these findings, the present invention has been completed.

Therefore, the present invention relates to (1) A stabilized pharmaceutical preparation which is coated with a coating agent comprising (i) an agent for the protection from light, said agent being capable of producing free radicals when exposed to ultraviolet rays, and (ii) a free radical scavenger;

(2) A pharmaceutical preparation as described in the above (1), wherein the coating agent further comprises an oily substance selected from the group consisting of an ester and an alcohol;

(3) A pharmaceutical preparation as described in the above (1), wherein the agent for the protection from light is a metal oxide;

(4) A pharmaceutical preparation as described in the above (3), wherein the metal oxide is a titanium oxide, ferric oxide or zinc oxide;

(5) A pharmaceutical preparation as described in the above (1), wherein the free radical scavenger is sulfites or vitamins;

(6) A pharmaceutical preparation as described in the above (5), wherein the vitamins are vitamin C or vitamin E;

(7) A pharmaceutical preparation as described in the above (2), wherein the oily substance is polyethylene glycol;

(8) A stabilized pharmaceutical preparation which is coated with a coating agent comprising (i) titanium oxide and (ii) sodium hydrogensulfite, ascorbic acid, sodium ascorbate, calcium ascorbate, dl-α-tocopherol or dl-α-tocopherol acetate;

(9) A pharmaceutical preparation as described in the above (2), wherein the coating agent further comprises a basic substance;

(10) A pharmaceutical preparation as described in the above (9), wherein the basic substance is a metal carbonate or a metal hydroxide;

(11) A stabilized pharmaceutical preparation which is coated with a coating agent comprising (i) an oily substance selected from the group consisting of an ester and an alcohol, and (ii) a free radical scavenger;

(12) A stabilized pharmaceutical preparation which is coated with a coating agent comprising (i) an oily substance selected from the group consisting of an ester and an alcohol, and (ii) a basic substance;

(13) A pharmaceutical preparation as described in the above (12), wherein the coating agent further comprises an agent for the protection from light, said agent being capable of producing free radicals when exposed to ultraviolet rays;

(14) A coating agent which comprises (i) an agent for the protection from light, said agent being capable of producing free radicals when exposed to ultraviolet rays, and (ii) a free radical scavenger;

(15) A method of stabilizing a pharmaceutical preparation which comprises coating a composition containing a drug with a coating agent comprising (i) an agent for the protection from light, said agent being capable of producing free radicals when exposed to ultraviolet rays, and (ii) a free radical scavenger;

(16) A method of stabilizing a pharmaceutical preparation which comprises coating a composition containing a drug with a coating agent comprising (i) an oily substance selected from the group consisting of an ester and an alcohol, and (ii) a free radical scavenger;

(17) A method of stabilizing a pharmaceutical preparation which comprises coating a composition containing a drug with a coating agent comprising (i) an oily substance selected from the group consisting of an ester and an alcohol, and (ii) a basic substance;

(18) Use of a coating agent which comprises (i) an agent for the protection from light, said agent being capable of producing free radicals when exposed to ultraviolet rays, and (ii) a free radical scavenger, for stabilizing a pharmaceutical preparation;

(19) Use of a coating agent which comprises (i) an oily substance selected from the group consisting of an ester and an alcohol, and (ii) a basic substance, for stabilizing a pharmaceutical preparation;

(20) Use of a coating agent which comprises (i) an oily substance selected from the group consisting of an ester and an alcohol, and (ii) a basic substance, for stabilizing a pharmaceutical preparation.

DETAILED DESCRIPTION OF THE INVENTION

"An agent for the protection from light, said agent being capable of producing free radicals when exposed to ultraviolet rays", "a free radical scavenger", "an oily substance selected from the group consisting of an ester and an alcohol", "a basic substance", "a coating agent" and "a pharmaceutical preparation" which are used in the present invention, are detailed hereafter.

"An agent for the protection from light, said agent being capable of producing free radicals when exposed to ultraviolet rays" means that the agent is added to a pharmaceutical preparation for the protection from light, and is capable of producing free radicals when exposed to ultraviolet rays. In general, the agent for the protection from light is a substance producing free radicals when exposed to light from a fluorescent lamp indoors or to sunlight outdoors, at normal temperatures. The free radical, for instance, includes HO., $HO_2.$, $O_2.^-$, etc.

Such an agent for the protection from light, for instance, includes a oxide of an inorganic compound such as titanium oxide, ferric oxide, zinc oxide, etc. The agent for the protection from light is preferably a metal oxide, further preferably titanium oxide. When titanium oxide is used, its particle size in diameter is generally approximately 0.01 to approximately 1.5 $\mu$m, preferably approximately 0.1 to approximately 0.7 $\mu$m.

The amount of "an agent for the protection from light, said agent being capable of producing free radicals when exposed to ultraviolet rays" in the coating agent can be any one that can accomplish a purpose of protecting a pharmaceutical preparation from light, for instance, approximately 5 to approximately 30 weight %, and preferably approximately 10 to approximately 30 weight %.

"A free radical scavenger" can be any one as long as it is a substance which is capable of scavenging the above mentioned free radicals, or suppresses decomposition of an ingredient in a coating agent or a pharmaceutical preparation by oxidation. A free radical scavenger includes, for instance, a sugar alcohol such as mannitol, etc.; an organic acid such as benzoic acid, etc.; an amino acid such as tryptophan, cysteine, etc.; a carbonate ion; a metal complex such as copper complex, manganese complex, etc.; a sulfite such as sodium hydrogensulfite, sodium sulfite, sodium metabisulfite, etc.; a thiol derivative such as sodium formaldehydesulfoxylate (rongalit), thioglycerol, etc.; a natural resin such as guaic oil, etc.; a phenol derivative such as nordihydroguaiaretic acid, propyl gallate, butylhydroxyanisole, dibutylhydroxytoluene, etc.; vitamins such as erythorbic acid, sodium erythorbate, vitamin C (e.g. an ester of ascorbic acid such as ascorbyl palmitate, ascorbyl dipalmitate, ascorbyl stearate, etc.; ascorbic acid; a salt of ascorbic acid such as sodium ascorbate, calcium ascorbate), vitamin E (e.g. an ester of tocopherol such as dl-$\alpha$-tocopherol succinate, d-$\alpha$-tocopherol succinate, dl-$\alpha$-tocopherol calcium succinate, dl-$\alpha$-tocopherol acetate, d-$\alpha$-tocopherol acetate, dl-$\alpha$-tocopherol nicotinate, etc.; dl-$\alpha$-tocopherol; d-$\alpha$-tocopherol; dl-$\delta$-tocopherol; d-$\delta$-tocopherol; natural vitamin E, etc.), $\beta$-carotene, etc.; a peptide such as glutathione, etc.; a purine derivative such as uric acid, etc.; etc. These free radical scavengers can be used singly or as a mixture of two or more in a given ratio.

"A free radical scavenger" is preferably a sulfite or vitamins (especially vitamin C or vitamin E), more preferably sodium hydrogensulfite, ascorbic acid, sodium ascorbate, calcium ascorbate, dl-$\alpha$-tocopherol or dl-$\alpha$-tocopherol acetate.

Ethylenediamine tetraacetic acid or a salt thereof, etc. also can be used in combination to increase the effect of "a free radical scavenger".

The amount of "a free radical scavenger" in the coating agent can be any one that can scavenge free radicals produced from "an agent for the protection from light, said agent being capable of producing free radicals when exposed to ultraviolet rays". The amount of "a free radical scavenger" in a coating agent is, for instance, approximately 0.1 to approximately 50% by weight, preferably approximately 1 to approximately 20% by weight.

"An oily substance selected from the group consisting of an ester and an alcohol" includes, for instance, an ester or an alcohol, preferably a polyvalent alcohol, etc, which are oily at approximately 20 to approximately 65° C. The oily substance can include a plasticizer which can be generally used in a pharmaceutical preparation, for instance, an ester such as triethyl citrate, medium chain fatty acid triglyceride, diethyl phthalate, dibutyl phthalate, triacetine (triacetyl glycerin), butylphthalyl butylglycolate, capryl glycerin, etc.; an alcohol such as a polyvalent alcohol (e.g. glycerin, propylene glycol, polyethylene glycol, etc.), etc. Furthermore, sesame oil, castor oil, etc., can be also used as an oily substance. These oily substances can be used singly or as a mixture of two or more in a given ratio.

The oily substance includes preferably an alcohol, more preferably a polyvalent alcohol, further more preferably polyethylene glycol. Polyethylene glycol includes, for instance, polyethylene glycol 400, polyethylene glycol 600, polyethylene glycol 1500, polyethylene glycol 4000, polyethylene glycol 6000, etc.

The amount of the oily substance in the coating agent is, for instance, approximately 0.1 to approximately 30% by weight, preferably approximately 10 to approximately 20% by weight.

A coating agent which has excellent strength, expandability and handling properties can be obtained by adding the above-mentioned oily substance to the coating agent. And a uniform coating is also facilitated by using these coating agents.

"A basic substance" can be any one as long as it is a substance showing basicity in neutralizing an acid such as formic acid, etc., and includes specifically a salt showing basicity such as metal carbonates, for instance, alkali metal hydrogencarbonates (e.g. sodium hydrogencarbonate, etc.), alkali metal carbonates (e.g. sodium carbonate, potassium carbonate, etc.), alkaline earth metal carbonates (e.g. calcium carbonate, magnesium carbonate, etc.), etc.; disalt hydrogenphosphates such as di-alkali metal hydrogenphosphates (e.g. disodium hydrogenphosphate, dipotassium hydrogenphosphate, etc.), etc.; silicates such as calcium silicate, magnesium silicate, etc.; metal oxides such as magnesium oxide, etc.; metal hydroxides such as sodium hydroxide, calcium hydroxide, magnesium hydroxide, aluminum hydroxide, etc.; citrates such as sodium citrate, etc.; tartrates such as DL- or L-sodium tartrate, etc.; pantothenates such as calcium pantothenate, etc; oxides or hydroxides. These basic substances can be used singly or as a mixture of two or more in a given ratio.

The basic substance is preferably a metal carbonate or a metal hydroxide, more preferably sodium hydrogencarbonate, sodium carbonate, potassium carbonate, calcium carbonate, magnesium carbonate, magnesium hydroxide.

The amount of the basic substance in the coating agent can be any one that can sufficiently neutralize an acid such as formic acid produced in a pharmaceutical preparation, for instance, approximately 0.1 to approximately 50% by weight, preferably approximately 1 to approximately 20% by weight.

"A coating agent" can comprise a coating material other than the above-mentioned "agent for the protection from light, said agent being capable of producing free radicals when exposed to ultraviolet rays", "free radical scavenger", "oily substance selected from the group consisting of an ester and an alcohol" or "basic substance". The amount of the coating material in the coating agent is one that is used for manufacturing a general preparation. If necessary "a coating agent" can further comprise an additive which does not interfere with the coating agent or the pharmaceutical preparation.

"A coating agent" can be a liquid in which each of the above-mentioned ingredients is dissolved or dispersed in water or organic solvent. The kinds of the organic solvent are not limited, and for instance, an alcohol such as methanol, ethanol, isopropyl alcohol, etc.; a ketone such as acetone, etc.; can be used. A mixture of water and organic solvent also can be used.

The above-mentioned coating material includes, for instance, a sugar coating material, a water soluble film-coating material, an enteric film-coating-material, a sustained release film-coating material, etc.

As the sugar coating material, sucrose can be used, and one, two or more of a group selected from talc, precipitated calcium carbonate, gelatin, acacia, pullulan, and carnauba wax, etc., can be used in combination.

The water soluble film-coating-material includes, for instance, cellulose polymers such as hydroxypropylcellulose, hydroxypropylmethylcellulose, hydroxyethylcellulose, methylhydroxyethylcellulose, etc.; a synthetic polymer such as polyvinylacetal diethylaminoacetate, aminoalkyl methacrylate copolymer E [EUDRAGIT E (trade name), Rohm Pharma Co.], polyvinylpyrrolidone, etc.; a polysaccharide such as pullulan, etc.; etc.

The enteric film-coating-material includes, for instance, cellulose polymers such as hydroxypropylmethylcellulose phthalate, hydroxypropylmethylcellulose acetate succinate, carboxymethylethylcellulose, cellulose acetate phthalate, etc.; acrylic acid polymers such as methacrylic acid copolymer L [EUDRAGIT L (trade name), Rohm Pharma Co.], methacrylic acid copolymer LD [EUDRAGIT L-30D55 (trade name), Rohm Pharma Co.], methacrylic acid copolymer S [EUDRAGIT S (trade name) Rohm Pharma Co.], etc.; natural compounds such as shellac, etc.; etc.

The sustained release film-coating-material includes, for instance, cellulose polymers such as ethylcellulose, etc.; acrylic acid polymers such as aminoalkyl methacrylate copolymer RS [EUDRAGIT RS (trade name), Rohm Pharma Co.], emulsion of ethyl acrylate and methyl methacrylate copolymer [EUDRAGIT NE (trade name), Rohm Pharma Co.], etc.; etc.

Two or more of the above-mentioned coating materials can be used as a mixture in a given ratio.

The above-mentioned additive includes, for instance, colorants, flavorants, etc., and can be added in the amount used in the manufacture of a general preparation.

The colorants include, for instance, a water soluble food tar dye (e.g. food red No.2 or No.3, food yellow No.4 or No.5, food blue No.1 or No.2, etc.), a water insoluble lake dye (an aluminum salt of the above-mentioned water soluble food tar dye, etc.), natural colorants (e.g. β-carotene, chlorophyll, etc.), etc.

The flavorants include, for instance, lemon oil, orange, dl- or l-menthol, etc.

"A coating agent" of the present invention can be manufactured, for instance, by mixing each ingredient of the above-mentioned "an agent for the protection from light, said agent being capable of producing free radicals when exposed to ultraviolet rays", "a free radical scavenger", "an oily substance selected from the group consisting of an ester and an alcohol" or "a basic substance", and the coating material, if necessary, after adding the above-mentioned additive.

"A coating agent" also can be manufactured by dissolving or dispersing each of the above-mentioned ingredients in water or the above-mentioned organic solvent. A uniform coating can be obtained by such manufacturing method.

"A pharmaceutical preparation" of the present invention can be obtained by coating "a composition containing a drug" with the above-mentioned coating agent. "A composition containing a drug" can be "a drug" alone or a mixture of "a drug" and a conventional "preparation ingredient" used for manufacturing a pharmaceutical preparation.

A dosage form of the composition containing a drug includes, for instance, tablets, powders, granules, fine granules, pills, etc.

"A drug" includes a drug decomposed when exposed to light, especially ultraviolet rays; a drug decomposed by free radicals; or a drug decomposed by an aldehyde (e.g. formaldehyde, acetaldehyde), an acid (e.g. formic acid) or a peroxide, which are produced as a consequence of decomposition of a preparation ingredient by free radicals. These drugs include, for instance, one or more agents selected from the group consisting of nourishing and health-promoting agents, antipyretic-analgesic-antiinflammatory agents, antipsychotic drugs, antianxiety drugs, antidepressants, hypnotic-sedatives, spasmolytics, central nervous system affecting drugs, cerebral metabolism ameliolators, antiepileptics, sympathomimetic agents, gastrointestinal function conditioning agents, antacids, antiulcer agents, antitussive-expectorants, antiemetics, respiratory stimulants, bronchodilators, antiallergic agents, dental buccal drugs, antihistamines, cardiotonics, antiarrhythmic agents, diuretics, hypotensive agents, vasoconstrictors, coronary vasodilators, peripheral vasodilators, antihyperlipidemic agents, cholagogues, antibiotics, chemotherapeutic agents, agents for treating diabetic, drugs for osteoporosis, skeletal muscle relaxants, antidinics, hormones, alkaloid narcotics, sulfa drugs, antipodagrics, anticoagulants, antimalignant tumor agents, agents for alzheimer's disease, etc.

The amount of "a drug" in "a pharmaceutical preparation" can be the effective amount of "a drug".

In the following, concrete examples of the above-mentioned drugs are described.

The nourishing and health-promoting agents include, for instance, vitamins such as vitamin A, vitamin D, vitamin E (d-α-tocopherol acetate, etc.), vitamin $B_1$ (dibenzoylthiamine, fursulthiamine hydrochloride, etc.), vitamin $B_2$ (riboflavin butyrate, etc.), vitamin $B_6$ (pyridoxine hydrochloride, etc.), vitamin C (ascorbic acid, sodium L-ascorbate, etc.), vitamin $B_{12}$ (hydroxocobalamin acetate, etc.), etc.; minerals such as calcium, magnesium and iron; proteins, amino acids, oligosaccharides, crude drugs, etc.

The antipyretic-analgesic-antiinflammatory agents include, for instance, aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous caffeine, serratiopeptidase, lysozyme chloride, tolfenamic acid, mefenamic acid, diclofenac sodium, flufenamic acid, salicylamide, aminopyrine, ketoprofen, indomethacin, bucolome, pentazocine, etc.

The antipsychotic drugs include, for instance, chlorpromazine, reserpine, etc.

The antianxiety drugs include, for instance, alprazolam, chlordiazepoxide, diazepam, etc.

The antidepressants include, for instance, imipramine, maprotiline, amphetamine, etc.

The hypnotic-sedatives include, for instance, estazolam, nitrazepam, diazepam, perlapine, phenobarbital sodium, etc.

The spasmolytics include, for instance, scopolamine hydrobromide, diphenhydramine hydrochloride, papaverine hydrochloride, etc.

The central nervous system affecting drugs include, for instance, citicoline, rotirenine, etc.

The cerebral metabolism ameliolators include, for instance, idevenone, vinpocetine, meclofenoxate hydrochloride, 8-[1-oxo-3-[1-(phenylmethyl)piperidine-4-yl]propyl]-2,3,4,5-tetrahydro-1H-1-benzazepine or a salt thereof, etc.

The antiepileptics include, for instance, phenytoin, carbamazepine, etc.

The sympathomimetic agents include, for instance, isoproterenol hydrochloride, etc.

The gastrointestinal function conditioning agents include, for instance, stomachic-digestives such as diastase, saccharated pepsin, scopolia extract, cellulase AP3, lipase AP, cinnamon oil, etc.; intestinal function controlling drugs such as perperine hydrochloride, resistant lactic acid bacterium, *Lactobacillus bifidus*, etc.

The antacids include, for instance, magnesium carbonate, sodium hydrogen carbonate, magnesium aluminometasilicate, synthetic hydrotalcite, precipitated calcium carbonate, magnesium oxide, etc.

The antiulcer agents include, for instance, benzimidazole compounds (e.g. lansoprazole, omeprazole, rabeprazole, pantoprazole), famotidine, cimetidine, ranitidine hydrochloride, etc.

The antitussive-expectorants include, for instance, chloperastine hydrochloride, dextromethorphan hydrobromide, theophylline, potassium guaiacolsulfonate, guaifenesin, codeine phosphate, etc.

The antiemetics include, for instance, diphenidol hydrochloride, metoclopramide, etc.

The respiratory stimulants include, for instance, levallorphan tartrate, etc.

The bronchodilators include, for instance, theophylline, salbutamol sulfate, etc.

The antiallergic agents include, for instance, amlexanox, seratrodast, etc.

The dental buccal drugs include, for instance, oxytetracycline, triamcinolone acetonide, chlorhexidine hydrochloride, lidocaine, etc.

The antihistamines include, for instance, diphenhydramine hydrochloride, promethazine, isothipendyl hydrochloride, dl-chlorpheniramine maleate, etc.

The cardiotonics include, for instance, caffeine, digoxin, etc.

The antiarryhythmic agents include, for instance, procainamide hydrochloride, propranolol hydrochloride, pindolol, etc.

The diuretics include, for instance, isosorbide, furosemide, etc.

The hypotensive agents include, for instance, delapril hydrochloride, captopril, hexamethonium bromide, hydralazine hydrochloride, labetalol hydrochloride, manidipine hydrochloride, candesartan cilexetil, methyldopa, losartan, valsartan, eprosartan, irbesartan, tasosartan, telmisartan, pomisarutan, ripisartan, forasartan, etc.

The vasoconstrictors include, for instance, phenylephrine hydrochloride, etc.

The coronary vasodilators include, for instance, carbocromen hydrochloride, molsidomine, verapamil hydrochloride, etc.

The peripheral vasodilators include, for instance, cinnarizine, etc.

The antihyperlipidemic agents include, for instance, cerivastatin sodium, simvastatin, pravastatin sodium, etc.

The cholagogues include, for instance, dehydrocholic acid, trepibutone, etc.

The antibiotics include, for instance, cephem antibiotics such as cefalexin, amoxicillin, pivinecillinam hydrochloride, cefotiam dihydrochloride, cefozopran hydrochloride, cefmenoxime hydrochloride, cefsluodin sodium, etc.; synthetic antibacterials such as ampicillin, cyclacillin, sulbenicillin sodium, nalidixic acid, enoxacin. etc.; monobactam antibiotics such as carumonam sodium; penem antibiotics, carbapenem antibiotics, etc.

The chemotherapeutic agents include, for instance, sulfamethizole hydrochloride, thiazosulfone, etc.

The agents for treating diabetes include, for instance, tolbutamide, voglibose, thiazoline derivatives (e.g. pioglitazone hydrochloride, troglitazone), 5-[[4-[2-(methyl-2-pyridinylamino)ethoxy]phenyl]methyl]-2,4-thiazolidinedione, acarbose, miglitol, emiglitate. etc.

The drugs for osteoporosis Include, for instance, ipriflavone, etc.

The skeletal muscle relaxants include, for instance, methocarbamol, etc.

The antidinics include, for instance, meclizine hydrochloride, dimenhydrinate, etc.

The agents for alzheimer's disease include, for instance, idebenone, vinpocetine, 8-[1-oxo-3-[1-(phenylmethyl) piperidine-4-yl]propyl]-2,3,4,5-tetrahydro-1H-1-benzazepine or a salt thereof, etc.

The hormones include, for instance, riothyroinine sodium, dexamethasone sodium phosphate, prednisolone, oxendolone, leuprorelin acetate, etc.

The alkaloid narcotics include, for instance, opium, morphine hydrochloride, ipecac, oxycodone hydrochloride, opium alkaloid hydrochlorides, cocaine hydrochloride, etc.

The sulfadrugs include, for instance, sulfanilamide, sufamethizole, etc.

The antipodagrics include, for instance, allopurinol, colchicine, etc.

The anticoagulants include, for instance, dicoumarol, etc.

The anti-malignant tumor agents include, for instance, 5-fluorouracil, uracil, mitomycin, etc.

Since "a drug" having an amino group or an imino group is susceptible to decomposition when exposed to ultraviolet rays; free radicals; or an aldehyde (e.g. formaldehyde, acetaldehyde), an acid (e.g. formic acid) or a peroxide, which are produced as a consequence of the decomposition of a preparation ingredient by free radicals, it is preferable to use "a drug" having an amino group or an imino group as "a drug".

"A drug" is more preferably a compound represented by the formula

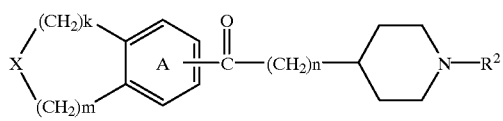

(I)

wherein X represents $R^1$—N<($R^1$ represents hydrogen, a hydrocarbon group which may be substituted or an acyl group which may be substituted), oxygen or sulfur; $R^2$ represents hydrogen or a hydrocarbon group which may be substituted; ring A represents a benzene ring which may be substituted; k represents an integer of 0 to 3; m represents an integer of 1 to 8; and n represents an integer of 1 to 6, or a salt thereof.

Referring to the above formula (I), "a hydrocarbon group" of "a hydrocarbon group which may be substituted" represented by $R^1$ and $R^2$ includes, for instance, a chain, a cyclic, a saturated or an unsaturated hydrocarbon group and a hydrocarbon group comprising various combinations of them. The chain saturated hydrocarbon group includes, for instance, a straight-chain or branched alkyl group which has 1 to 11 carbons ($C_{1-11}$) (e.g. methyl, ethyl, propyl, isopropyl, butyl, isobutyl, tert-butyl, pentyl, hexyl).

The chain unsaturated hydrocarbon group includes, for instance, a straight-chain or branched $C_{2-4}$ alkenyl group (e.g. vinyl, allyl, 2-butenyl, isopropenyl) and a $C_{2-4}$ alkynyl group (e.g. ethynyl, 2-propynyl, 2-butynyl, 3-butynyl).

The cyclic saturated hydrocarbon group includes $C_{3-7}$ monocyclic cycloalkyl group (e.g. cyclopropyl, cyclobutyl, cyclopentyl or cyclohexyl) and $C_{8-14}$ bridged cyclic saturated hydrocarbon group (e.g. bicyclo[3.2.1]oct-2-yl, bicyclo[3.3.1]non-2-yl, adamantan-1-yl).

The cyclic unsaturated hydrocarbon group includes phenyl group, or naphthyl group, etc.

The above-mentioned "hydrocarbon group" may also be a hydrocarbon group comprising various combinations of the above-exemplified chain, cyclic, saturated or unsaturated hydrocarbon groups including, for instance, $C_{7-18}$ aralkyl (e.g. tolyl, xylyl; phenyl-$C_{1-12}$ alkyl such as benzyl, phenethyl, phenylpropyl, phenylbutyl, phenylpentyl, phenylhexyl, etc.; α-naphthyl-$C_{1-8}$ alkyl such as α-naphthylmethyl, etc.), $C_{8-18}$ arylalkenyl (e.g. phenyl-$C_{2-12}$ alkenyl such as styryl, cinnamyl, 4-phenyl-2-butenyl, 4-phenyl-3-butenyl), $C_{8-18}$ arylalkynyl (e.g. phenyl-$C_{2-12}$ alkynyl such as phenylethynyl, 3-phenyl-2-propynyl, 3-phenyl-1-propynyl), $C_{3-7}$ cycloalkyl-$C_{1-6}$ alkyl (e.g. cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl or cycloheptylhexyl), etc.

"A hydrocarbon group" of "a hydrocarbon group which may be substituted" represented by $R^1$ is preferably, among the above-mentioned examples, a straight-chain or branched $C_{1-7}$ alkyl group (e.g. methyl, ethyl, propyl, isopropyl, butyl, isobutyl, sec-butyl, tert-butyl, pentyl, isopentyl, hexyl, heptyl) or $C_{7-10}$ aralkyl (e.g. benzyl, phenethyl, phenylpropyl), etc.

"A hydrocarbon groups" of "a hydrocarbon group which may be substituted" represented by $R^2$ is preferably, in the above-mentioned examples, $C_{7-10}$ aralkyl (e.g. benzyl, phenethyl, phenylpropyl), etc.

The above-mentioned hydrocarbon represented by $R^1$ or $R^2$ can have a substituent at its substitutable positions.

A substituent on the above-mentioned chain saturated, chain unsaturated or cyclic saturated hydrocarbon groups represented by $R^1$ or $R^2$ includes, for instance, halogen atom (e.g. fluorine, chlorine, bromine, iodine), nitro group, cyano group, hydroxy group, $C_{1-4}$ alkoxy group (e.g. methoxy, ethoxy, propyloxy, butyloxy, isopropyloxy), $C_{1-4}$ alkylthio group (e.g. methylthio, ethylthio, propylthio, isopropylthio, buthylthio), amino, mono- or di-$C_{1-4}$ alkylamino group (e.g. methylamino, ethylamino, propylamino, dimethylamino, diethylamino), cyclic amino group (e.g. pyrrolidino, piperidino), morpholino, $C_{1-4}$ alkyl-carbonylamino group (e.g. alkyl-carbonylamlno, wherein the alkyl portion is $C_{1-4}$, such as acetylamino, propionylamino, butyrylamino, etc.), $C_{1-4}$ alkylsulfonylamino group (e.g. methylsulfonylamino, ethylsulfonylamino), $C_{1-4}$ alkoxy-carbonyl group (e.g. methoxycarbonyl, ethoxycarbonyl, propoxycarbonyl), hydroxycarbonyl group, $C_{1-6}$ alkyl-carbonyl group (e.g. acetyl, propionyl, butyryl, valeryl, heptanoyl), carbamoyl, mono- or di-$C_{1-4}$ alkyl-carbamoyl group (e.g. N-methylcarbamoyl, N-ethylcarbamoyl, N-propylcarbamoyl, N-butylcarbamoyl), $C_{1-6}$ alkylsulfonyl group (e.g. methylsulfonyl, ethylsulfonyl, propylsulfonyl), etc. The hydrocarbon group can be substituted by 1 to 5 groups selected from the above-mentioned substituents.

A substituent of "a benzene ring which may be substituted" represented by ring A, or a substituent of a cyclic unsaturated hydrocarbon group represented by $R^1$ or $R^2$ in the formula (I) includes, for example, $C_{1-4}$ alkyl group (e.g. methyl, ethyl, propyl, butyl), halogen atom (e.g. fluorine, chlorine, bromine, iodine), nitro, cyano, hydroxy, $C_{1-4}$ alkoxy group (e.g. methoxy, ethoxy, propyloxy, butyloxy, isopropyloxy), $C_{1-4}$ alkylthio group (e.g. methylthio, ethylthio, propylthio, isopropylthio, butylthio), amino group, mono- or di-$C_{1-4}$ alkylamino group (e.g. N-methylamino, N-ethylamino, N-propylamino, N,N-dimethylamino, N,N-diethylamino), cyclic amino group (e.g. pyrrolidino, piperidino), morpholino, $C_{1-4}$ alkyl-carbonylamino group (e.g. acetylamino, propionylamino, butyrylamino), aminocarbonyloxy group, mono- or di-$C_{1-4}$ alkylcarbamoyloxy group (e.g. N-methylcarbamoyloxy, N-ethylcarbamoyloxy, N,N-dimethylcarbamoyloxy, N,N-diethylcarbamoyloxy), $C_{1-4}$ alkylsulfonylamino group (e.g. methylsulfonylamino, ethylsulfonylamino, propylsulfonylamino), $C_{1-4}$ alkoxy-carbonyl group (e.g. methoxycarbonyl, ethoxycarbonyl, propoxycarbonyl, isobutoxycarbonyl), carboxy group, $C_{1-6}$ alkyl-carbonyl group (e.g. acetyl, propionyl, butyryl, cyclohexylcarbonyl), carbamoyl, mono- or di-$C_{1-4}$ alkyl-carbamoyl group (e.g. N-methylcarbamoyl, N-ethylcarbamoyl, N-propylcarbamoyl, N-butylcarbamoyl, N,N-diethylcarbamoyl, N,N-dibutylcarbamoyl), $C_{1-6}$ alkylsulfonyl group (e.g. methylsulfonyl, ethylsulfonyl, propylsulfonyl, cyclopentylsulfonyl, cyclohexylsulfonyl); a phenyl, naphthyl, phenoxy, benzoyl, phenoxycarbonyl, phenyl$C_{1-4}$ alkylcarbamoyl, phenylcarbamoyl, phenyl$C_{1-4}$ alkylcarbonylamino, benzoylamino, phenyl$C_{1-4}$ alkylsulfonyl, phenylsulfonyl, phenyl$C_{1-4}$ alkylsulfinyl, phenyl$C_{1-4}$ alkylsulfonylamino or phenylsulfonylamino group which can have 1 to 4 substituents (a substituent in each phenyl group or naphthyl group includes, for instance, $C_{1-4}$ alkyl group, $C_{1-4}$ alkoxy group, halogen atom such as fluorine, chlorine, bromine and iodine, hydroxy group, benzyloxy group, amino group, mono- or di-$C_{1-4}$ alkylamino group, nitro group, $C_{1-4}$ alkyl-carbonyl group, etc., which are mentioned in the above). The suitable number of substituents on the "benzene ring which may be substituted" represented by ring A, or the cyclic unsaturated hydrocarbon group represented by $R^1$ or $R^2$, are approximately 1 to 3.

A substituent of a hydrocarbon group comprising various combinations of a chain, a cyclic, a saturated and an unsaturated, hydrocarbon group represented by $R^1$ or $R^2$ includes, for instance, $C_{1-4}$ alkyl group (e.g. methyl, ethyl, propyl, butyl), halogen atom (e.g. fluorine, chlorine, bromine, iodine), nitro group, cyano group, hydroxy group, $C_{1-4}$ alkoxy group (e.g. methoxy, ethoxy, propyloxy, butyloxy, isopropyloxy), $C_{1-4}$ alkylthio group (e.g. methylthio, ethylthio, propylthio, isopropylthio, butylthio), amino group, mono- or di-$C_{1-4}$ alkylamino group (e.g. N-methylamino, N-ethylamino, N-propylamino, N,N-dimethylamino, N,N-diethylamino), cyclic amino group (e.g. pyrrolidino, piperidino), morpholino, $C_{1-4}$ alkylcarbonylamino group (e.g. acetylamino, propionylamino, butyrylamino), carbamoyloxy group, mono- or di-$C_{1-4}$ alkylcarbamoyloxy group (e.g. N-methylcarbamoyloxy, N-ethylcarbamoyloxy, N,N-dimethylcarbamoyloxy, N,N-diethylcarbamoyloxy), $C_{1-4}$ alkylsulfonylamino group (e.g. methylsulfonylamino, ethylsulfonylamino, propylsulfonylamino), $C_{1-4}$ alkoxy-carbonyl group (e.g. methoxycarbonyl, ethoxycarbonyl, propoxycarbonyl, isobutoxycarbonyl), hydroxycarbonyl group, $C_{1-6}$ alkyl-carbonyl group (e.g. acetyl, propionyl, butyryl, cyclohexylcarbonyl), carbamoyl group, mono- or di-$C_{1-4}$ alkyl-carbamoyl group (e.g. N-methylcarbamoyl, N-ethylcarbamoyl, N-propylcarbamoyl, N-butylcarbamoyl, N,N-diethylcarbamoyl, N,N-dibutylcarbamoyl), $C_{1-6}$ alkylsulfonyl group (e.g. methylsulfonyl, ethylsulfonyl, propylsulfonyl, cyclopentylsulfonyl, cyclohexylsulfonyl); aphenyl, naphthyl, phenoxy, benzoyl, phenoxycarbonyl, phenyl$C_{1-4}$ alkylcarbamoyl, phenylcarbamoyl, phenyl$C_{1-4}$ alkylcarbonylamino, benzoylamino, phenyl$C_{1-4}$ alkylsulfonyl, phenylsulfonyl, phenyl$C_{1-4}$ alkylsulfinyl, phenyl$C_{1-4}$ alkylsulfonylamino or phenylsulfonylamino group which can have 1 to 4 substituents (a substituent on each cyclic group includes, for instance, $C_{1-4}$ alkyl group such as methyl, ethyl, propyl, isopropyl, $C_{1-4}$ alkoxy group such as methoxy, ethoxy, propyloxy, isopropyloxy or butyloxy, halogen atom such as fluorine, chlorine, bromine and iodine, hydroxy group, benzyloxy group, amino group, mono- or di-$C_{1-4}$ alkyl-substituted amino group such as the above-mentioned one, nitro, $C_{1-4}$ alkylcarbonyl such as the above-mentioned one, etc.). The number of substituents in these "hydrocarbon groups comprising various combinations" are preferably approximately 1 to 5.

The "acyl group" of the "acyl group which may be substituted" represented by $R^1$ includes, for instance, carboxylic acid-derived acyl group (e.g. formyl, $C_{2-8}$ alkyl-carbonyl or phenyl carbonyl such as acetyl, propionyl, butyryl, benzoyl, etc.), sulfonic acid-derived acyl group (e.g. $C_{1-7}$ alkylsulfonyl or phenylsulfonyl such as methanesulfonyl, ethanesulfonyl, propanesulfonyl, benzene sulfonyl, p-toluenesulfonyl, etc.), phosphoric acid-derived acyl group (e.g. $C_{1-7}$ alkylphosphonyl or phenylphosphonyl such as methanephosphonyl, ethanephosphonyl, propanephosphonyl, benzene phosphonyl, etc.), and substituted oxycarbonyl group (e.g. $C_{1-8}$ alkoxy-carbonyl or $C_{7-8}$ aralkyloxy-carbonyl such as ethoxycarbonyl, tert-butoxycarbonyl, benzyloxycarbonyl, etc.). Among these groups, a $C_{2-8}$ alkyl-carbonyl group is preferable.

These acyl groups may be substituted with, for example, halogen atom (e.g. fluorine, chlorine, bromine, iodine), amino, mono- or di- alkylamino group which have $C_{1-6}$ alkyl group (e.g. methyl, ethyl, propyl, hexyl), $C_{1-4}$ alkoxy group (e.g. methoxy, ethoxy, propyloxy), etc. These acyl groups can have 1 to 3, preferably 1 to 2 of these substituents at its substitutable positions.

The preferable embodiments of the compound represented by formula (I) (it may be abbreviated merely as compound (I) in this specification) are described in the following.

X is preferably $R^1$—N<, and more preferably the case where $R^1$ is hydrogen, a straight-chain or branched $C_{1-3}$ alkyl (e.g. methyl, ethyl, propyl, isopropyl), benzyl, phenyl, $C_{1-4}$ alkyl-carbonyl (e.g. acetyl, propionyl, butyryl), benzoyl, $C_{1-4}$ alkoxy-carbonyl (e.g. methoxycarbonyl, ethoxycarbonyl), etc. X is further more preferably HN<.

$R^2$ is preferably a benzyl or α-naphthylmethyl group which may optionally be substituted by 1 or 2 halogen atoms (e.g. fluorine, chlorine), methyl, nitro and/or methoxy, and is more preferably unsubstituted benzyl.

The substituent (s) on ring A are preferably fluorine, chlorine, trifluoromethyl, methyl, methoxy, etc., more preferably fluorine. And k and m are preferably such that the sum of k and m (k+m) is an integer of 2 to 6, that is to say,

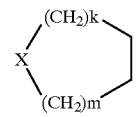

is a 5- to 9-membered ring preferably, k+m is 4. Preferred specific combinations of k and m are such that when k is 0, m is 2, 3, 4, or 5; when k is 1, m is 1, 2, or 3; and when k is 2, m is 2. That is to say, the nitrogen-containing condensed heterocyclic ring of the formula:

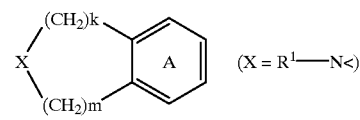

preferably includes 2,3-dihydro-1H-indole, 1,2,3,4-tetrahydroquinoline, 2,3,4,5-tetrahydro-1H-1-benzazepine, 2,3-dihydro-1H-isoindole, 1,2,3,4-tetrahydroisoquinoline, 2,3,4,5-tetrahydro-1H-2-benzazepine, 2,3,4,5-tetrahydro-1H-3-benzazepine, 1,2,3,4,5,6-hexahydro-1-benzazocine, 1,2,3,4,5,6-hexahydro-2-benzazocine, 1,2,3,4,5,6-hexahydro-3-benzazocine, 2,3,4,5,6,7-hexahydro-1H-1-benzazonine, 2,3,4,5,6,7-hexahydro-1H-2-benzazonine, 2,3,4,5,6,7-hexahydro-1H-3-benzazonine, 2,3,4,5,6,7-hexahydro-1H-4-benzazonine.

The oxygen-containing condensed heterocyclic ring of the formula:

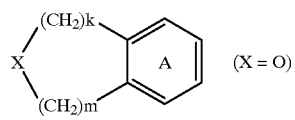   (X = O)

preferably includes 2,3-dihydrobenzofuran, 1,3-dihydroisobenzofuran, 3,4-dihydro-2H-1-benzopyran, 3,4-dihydro-1H-2-benzopyran, 2,3,4,5-tetrahydro-1-benzoxepine, 1,3,4,5-tetrahydro-2-benzoxepine, 1,2,4,5-tetrahydro-3-benzoxepine, 3,4,5,6-tetrahydro-2H-1-benzoxocine, 3,4,5,6-tetrahydro-1H-2-benzoxocine, 1,4,5,6-tetrahydro-2H-3-benzoxocine, 2,3,4,5,6,7-hexahydro-1-benzoxonine, 1,3,4,5,6,7-hexahydro-2-benzoxonine, 1,2,4,5,6,7-hexahydro-3-benzoxonine, 1,2,3,5,6,7-hexahydro-4-benzoxonine, etc.

The sulfur-containing condensed heterocyclic ring of the formula:

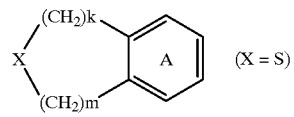   (X = S)

preferably includes 2,3-dihydro[b]thiophene, 1,3-dihydrobenzo[c]thiophene, 3,4-dihydro-2H-1-benzothiopyran, 3,4-dihydro-1H-2-benzothiopyran, 2,3,4,5-tetrahydro-1-benzothiepine, 1,3,4,5-tetrahydro-2-benzothiepine, 1,2,4,5-tetrahydro-3-benzothiepine, 3,4,5,6-tetrahydro-2H-1-benzothiocine, 3,4,5,6-tetrahydro-1H-2-benzothiocine, 1,4,5,6-tetrahydro-2H-3-benzothiocine, 2,3,4,5,6,7-hexahydro-1-benzothionine, 1,3,4,5,6,7-hexahydro-2-benzothionine, 1,2,4,5,6,7-hexahydro-3-benzothionine, and 1,2,3,5,6,7-hexahydro-4-benzothionine, etc.

The preferred condensed heterocyclic ring of the formula:

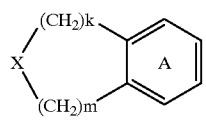

includes, for instance, a nitrogen-containing condensed heterocyclic ring represented by the formulae:

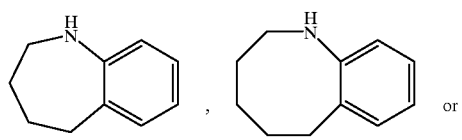 or

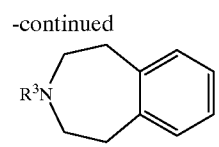

[wherein $R^3$ represents a hydrogen atom or a $C_{1-3}$ alkyl group], more preferably benzazepine ring. In the above-mentioned formulae, the $C_{1-3}$ alkyl group represented by $R^3$ is methyl, ethyl, propyl, isopropyl. n is preferably 1, 2, or 3, and is more preferably 2.

The compound (I) is further preferably 8-[1-oxo-3-[1-(phenylmethyl)piperidine-4-yl]propyl]-2,3,4,5-tetrahydro-1H-1-benzazepine.

The salt of Compound (I) is more preferably a physiologically acceptable acid addition salt. These salts include, for instance, salts with inorganic acids (e.g. hydrochloric acid, phosphoric acid, hydrobromic acid, sulfuric acid) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). When the compound (I) has an acidic group such as —COOH, the compound (I) may form salts with inorganic bases (e.g. sodium, potassium, calcium, magnesium, ammonia) or organic bases (e.g. triethylamine). The salt of Compound (I) is further more preferably a salt with an organic acid.

Compound (I) or a salt thereof is further more preferably 8-[1-oxo-3-[1-(phenylmethyl)piperidine-4-yl]propyl]-2,3,4,5-tetrahydro-1H-1-benzazepine fumarate.

Compound (I) or a salt thereof can be manufactured in accordance with a known method described in JP-A-5-140149 or a method analogous thereto.

The above-mentioned conventional "preparation ingredient" includes, for instance, excipients [e.g. lactose, sucrose, D-mannitol, D-sorbitol, starch (corn starch, potato starch, etc.), pregelatinized starch, dextrin, crystalline cellulose, low-substituted hydroxypropylcellulose, carboxymethylcellulose sodium, acacia, dextran, pullulan, light anhydrous silicic acid, synthetic aluminum silicate, magnesium aluminometasilicate, etc.], binders (e.g. pregelatinized starch, sucrose, gelatin, powdered acacia, methylcellulose, carboxymethylcellulose, carboxymethylcellulose sodium, hydroxypropylcellulose, hydroxypropylmethylcellulose, polyvinylpyrrolidone, crystalline cellulose, dextrin, pullulan, etc.), lubricants (e.g. magnesium stearate, calcium stearate, talc, colloidal silica, etc.), disintegrators [e.g. lactose, sucrose, carboxymethylcellulose, low-substituted hydroxypropylcellulose, starch (corn starch, potato starch, etc.), light anhydrous silicic acid, croscarmellose sodium, sodium carboxymethyl starch, carboxymethyl cellulose calcium, etc.], colorants, flavorants, corrigents, adsorbents, preservatives, wetting agents, antistatic agents, disintegration retarders, etc.

The added amount of the above-mentioned preparation ingredient can be one that is used for manufacturing a general preparation.

The dosage form of "a pharmaceutical preparation" of the present invention includes, for instance, tablets, powders, granules, fine granules, pills, etc. The granules include, for instance, at least approximately 90% by weight of the granules sized approximately 500 to approximately 1410 µm in particle diameter and at most approximately 5% by weight of the granules sized at most approximately 177 µm in particle diameter. The fine granules include also, for instance, at least approximately 75% by weight of the granules sized approximately 10 to approximately 500 μm in particle diameter, at most approximately 5% by weight of the granules sized at least approximately 500 μm in particle diameter and at most approximately 10% by weight of the granules sized at most approximately 10 μm in particle diameter. The fine granules include preferably at least approximately 75% by weight of the granules sized approximately 105 to approximately 500 μm in particle diameter, at most approximately 5% by weight of granules sized at least approximately 500 μm in particle diameter and at most approximately 10% by weight of the granules sized at most approximately 74 μm in particle diameter.

"A pharmaceutical preparation" of the present invention can be manufactured by coating "a composition containing a drug" obtained by mixing the above-mentioned "drug" and "preparation ingredient" in accordance with a conventional method, with "a coating agent".

The amount of the coating agent used can be selected depending on the dosage form of the pharmaceutical preparation. The amount of the coating agent used (dry weight) in a pharmaceutical preparation is, for instance, approximately 0.1 to approximately 30% by weight, preferably approximately 0.5 to approximately 10% by weight in the case of tablets; approximately 0.1 to approximately 50% by weight, preferably approximately 1 to approximately 20% by weight in the case of granules or pills; approximately 0.1 to approximately 100% by weight, preferably approximately 1 to approximately 50% by weight in the case of fine granules.

As coating methods, per se known methods such as pan coating, fluidized-bed coating, agitating fluidized-bed coating, or a combination of these procedures can be employed. When the coating agent is a solution or a dispersion, containing water or an organic solvent, spray-coating can also be employed.

Temperature during coating is generally approximately 25 to approximately 60° C., preferably approximately 25 to approximately 40° C.

And the time used for coating can be selected suitably taking into account the coating method, characteristics or amount of the coating agent or characteristics of the pharmaceutical preparation, etc.

The "pharmaceutical preparation" of the present invention can be used, for instance, when Compound (I) or a salt thereof is used as a drug, for the prophylaxis or treatment of diseases such as senile dementia, Alzheimer's disease, Huntington's chorea, hyperkinesia or mania, etc.

The dosage range of "a pharmaceutical preparation" of the present invention can be selected from the active range of the drug, taking into account the kind of drug, the kind of disease, conditions, formulations, etc. For instance, when Compound (I) or a salt thereof is used as a drug, "a pharmaceutical preparation" can be administered 1 or 2 to 3 times per day in the range of approximately 0.01 mg to approximately 100 mg, preferably approximately 0.1 to approximately 30 mg, more preferably 0.3 to 10 mg of Compound (I) or a salt thereof per day to an adult (body weight: 60 kg).

Various "pharmaceutical preparations" of the present invention are described specifically, as follows.

"A stabilized pharmaceutical preparation which is coated with the coating agent comprising an agent for the protection from light, said agent being capable of producing free radicals when exposed to ultraviolet rays, and a free radical scavenger" can be manufactured by coating the above-mentioned "composition containing a drug" with a coating agent comprising "an agent for the protection from light, said agent being capable of producing free radicals when exposed to ultraviolet rays" and "a free radical scavenger".

The coating agent preferably further comprises the oily substance selected from the group consisting of an ester and an alcohol. In this case, the coating agent preferably further comprises the basic substance. And the oily substance is preferably polyethylene glycol.

The preferable embodiment of "a pharmaceutical preparation" includes "a stabilized pharmaceutical preparation which is coated with the coating agent comprising (i) titanium oxide and (ii) sodium hydrogensulfite, asorbic acid, sodium ascorbate, calcium ascorbate, dl-α-tocopherol or dl-α-tocopherol acetate".

And the coating agent comprising "an agent for the protection from light, said agent being capable of producing free radicals when exposed to ultraviolet rays" and "a free radical scavenger", for instance, can be manufactured by dissolving or dispersing the ingredients with the coating materials in purified water.

"A stabilized pharmaceutical preparation which is coated with a coating agent comprising an oily substance selected from the group consisting of an ester and an alcohol, and a free radical scavenger" can be manufactured by coating the above-mentioned "composition containing a drug" with the coating agent comprising "an oily substance selected from the group consisting of an ester and an alcohol" and "a free radical scavenger".

And the coating agent comprising "a coating agent comprising an oily substance selected from the group consisting of an ester and an alcohol" and "a free radical scavenger" can be manufactured, for instance, by dissolving or dispersing these ingredients with the coating materials in purified water.

"The stabilized pharmaceutical preparation which is coated with a coating agent comprising an oily substance selected from the group consisting of an ester and an alcohol, and a basic substance" can be manufactured by coating the above-mentioned "composition containing a drug" with a coating agent comprising "an oily substance selected from the group consisting of an ester and an alcohol" and "a basic substance".

The coating agent is preferably further comprising an agent for the protection from light, said agent being capable of producing free radicals when exposed to ultraviolet rays.

And the coating agent comprising "a coating agent comprising an oily substance selected from the group consisting of an ester and an alcohol" and "a basic substance" can be manufactured, for instance, by dissolving or dispersing these ingredient with the coating materials in purified water.

BEST MODE FOR CARRYING OUT THE INVENTION

In the following, the present invention is illustrated specifically by Examples and Experimental Examples.

EXAMPLE 1

Each coating agent was manufactured by dissolving 129.6 g of hydroxypropylmethylcellulose 2910 (TC-5) and 30.0 g of polyethylene glycol 6000 in 2300 g of purified water, and then dispersing in 20.0 g of titanium oxide, 0.4 g of yellow ferric oxide and 20.0 g of a free radical scavenger or a basic substance represented in [Table 1] (In the following, they are abbreviated as Stabilizers.).

TABLE 1

Stabilizers a free radical scavenger sodium hydrogensulfite
ascorbic acid
d-α-tocopherol a basic substance sodium hydrogencarbonate

EXAMPLE 2

A coating agent is manufactured by dissolving 121.6 g of hydroxypropylmethylcellulose 2910 (TC-5) and 30.0 g of polyethylene glycol 6000 in 2300 g of purified water, and then dispersing in 20.0 g of titanium oxide, 0.4 g of yellow ferric oxide and 14.0 g of sodium hydrogensulfite and 14.0 g sodium hydrogencarbonate.

EXAMPLE 3

In a fluidized-bed granulating dryer (FD-3S, POWREX), 40.0 g of 8-[1-oxo-3-[1-(phenylmethyl)piperidine-4-yl]propyl]-2,3,4,5-tetrahydro-1H-1-benzazepine fumarate (In the following, it is abbreviated as Compound A.), 1600 g of mannitol and 220.0 g of corn starch were mixed uniformly. In the dryer, granulation was carried out while spraying an aqueous solution in which 60.0 g of hydroxypropylcellulose (HPC—L) was dissolved, to the mixture, and then drying was carried out in the fluidized-bed granulating dryer.

When obtained granules were crushed by a Power-Mill pulverizer (P-3, Showa Machinery Co., Ltd.) with a punching screen of 1.5 mm φ, comminuted powders were obtained.

Furthermore, comminuted powders were obtained by repeating the same operation as the above-mentioned one. To 3456.0 g of these comminuted powders, 126.0 g of corn starch and 18.0 g of magnesium stearate were added, which were mixed in a tumble mixer (TM-15, Showa Machinery Co., Ltd.) to yield granules for tabletting. Plain tablets were obtained by tabletting these granules with a rotary tabletting machine (Correct 19K, Kikusui Seisakusho Co., LTD.) with a punch of 6.5 mm φ at the weight of 100.0 mg (tabletting pressure: 0.8 ton/punch).

Various coating agents manufactured in Example 1 were sprayed onto the obtained plain tablets in a film-coating-machine (HCT-20, Freund Indusrrial Co. Ltd.) to yield 2800 of film-coating-tables prescribed in accordance with [Table 2] and containing 2.0 g of Compound A per tablet.

TABLE 2

Prescription of tablets (Ingredient per tablet):

| Ingredient | Incorporated amount (mg) |
|---|---|
| Compound A | 2.0 |
| D-mannitol | 80.0 |
| corn starch | 14.5 |
| hydroxypropylcellulose | 3.0 |
| magnesium stearate | 0.5 |
| Total (Plain tablet) | 100.0 |
| Plain tablet | 100.0 |

TABLE 2-continued

Prescription of tablets (Ingredient per tablet):

| Ingredient | Incorporated amount (mg) |
|---|---|
| (The film ingredients) | |
| hydroxypropylmethylcellulose 2910 | 2.592 |
| polyethylene glycol 6000 | 0.6 |
| titanium oxide | 0.4 |
| yellow ferric oxide | 0.008 |
| Stabilizers | 0.4 |
| Total | 104.0 |

EXAMPLE 4

Film-coated tablets are manufactured in substantially the same manner as in Example 3 except for using the coating agent manufactured in Example 2 as a coating agent.

COMPARATIVE EXAMPLE 1

Film-coated tablets were manufactured in substantially the same manner as Example 3 except that stabilizers were not used and hydroxypropylmethylcellulose 2910 (TC-5) was used in an amount of 2.992 mg per tablet.

EXPERIMENTAL EXAMPLE 1

Test to estimate stability of film-coated tablets

Film-coated tablets manufactured in Example 3 and Comparative Example 1 were put into a plastic petri dish. The upper side of the petri dish was covered with polyvinylidene chloride film (Saran Wrap, Asahi Chemical Industry Co., Ltd.), and the circumference of the petri dish was fixed with cellophane tape for complete sealing. After light-irradiation [Light source: white fluorescent lamp, Irradiation dose: 1,200,000 lux·hours (1000 lux×50 days)] to this petri dish, the produced amount of 1-methyl-8-[1-oxo-3-[1-(phenylmethyl)piperidine-4-yl]propyl]-2,3,4,5-tetrahydro-1H-1-benzazepine fumarate (In the following, it is abbreviated as Decomposed Compound I) which was produced by decomposition of Compound A and formaldehyde which was produced by decomposition of polyethylene glycol were measured in accordance with the following method.

[Quantificational method of Decomposed Compound I]

Compound A was dissolved in the mobile phase at the concentration of approximately 200 μg/ml. After filtration with a nonaqueous-filter (0.45 μm), quantification was carried out by high precision liquid chromatography (HPLC) method in the following conditions. The produced amount was described as the ratio to initial content of Compound A.

HPLC condition

Detector: ultraviolet rays absorption photometer,

Wavelength for measurement: 245 nm

Column: TSK gel-80Ts, Inside diameter: 4.6 mm, Length: 150 mm

Column temperature: 40° C.

Mobile phase: mixture of 0.05 M potassium dihydrogenphosphate solution (pH 3.0) and acetonitrile (volume ratio=2:1)

Flow rate: 1 ml/minute

Retention time: approximately 20 minutes

[Quantificational Method of Formaldehyde]

Five tablets were added to 50 ml of distilled water, which was shaken for 30 minutes to obtain a solution. The solution was centrifuged at 4000 rpm for 10 minutes. The filtrate which was obtained by filtration of the supernatant with an aqueous-filter (0.45 µm) was subjected to colorimetry (wavelength for measurement 550 nm) with Formaldehyde-Quantification-Kit (FORMALDEHYDE TEST WAKO, Wako Pure chemical Co., Ltd.).

The Decomposed Compound I has the following physical properties.

Chemical formula: $C_{26}H_{34}N_2O$

Molecular weight: 390.267

The results are shown in [Table 3]. In the table, ND means not detected. The detection limit of Decomposed Compound I which is a product by decomposition of Compound A is 0.05%. The detection limit of formaldehyde is 4 µg/tablet.

TABLE 3

| Stabilizers | Product amount of Decomposed Compound I (%) | Amount of formaldehyde (µg/tablet) |
| --- | --- | --- |
| The Present Invention (Example 3) | | |
| sodium hydrogensulfite | ND | 6 |
| ascorbic acid | ND | ND |
| d-α-tocopherol | ND | 6 |
| sodium hydrogencarbonate | ND | 24 |
| Control (Comparative Example 1) | | |
| none | 5.3 | 131 |

As shown in [Table 3], production of Decomposed Compound I and formaldehyde were suppressed by employing stabilizers. That is to say, decomposition of Compound A in the plain tablet coated with the coating agent was restrained, and produced amount of formaldehyde which interfered with Compound A was also suppressed by employing a coating agent comprising titanium oxide, polyethylene glycol 6000 and stabilizers.

EXPERIMENTAL EXAMPLE 2

Evaluation test of the influence on Compound A by a basic substance or a free radical scavenger Powders were obtained by mixing Compound A, titanium oxide, polyethylene glycol 6000, corn starch and stabilizers in the weight ratio of 0.3:5:5:2.5:2.5. The basic substance such as sodium hydrogencarbonate, sodium carbonate, calcium carbonate, magnesium carbonate, magnesium hydroxide; or the free radical scavenger such as d-α-tocopherol was used as stabilizers.

Powders used as control were obtained in substantially the same manner as the above-mentioned one except that corn starch was substituted for stabilizer.

The manufactured powders were put in to a glass petri dish. The upper side of the petri dish was covered with polyvinylidene chloride film (Saran Wrap, Asahi Chemical Industry Co., Ltd.), and circumference of the petri dish was fixed with cellophane tape for complete sealing. After light-irradiation [Light source: near UV fluorescent lamp, Irradiation dose: 350 µW/cm²×5 days] to this petri dish, the produced amount of Decomposed Compound I was measured in substantially the same manner as in Experimental Example 1.

The results are shown in [Table 4].

TABLE 4

| | stabilizers | Product amount of Decomposed Compound I (%) |
| --- | --- | --- |
| The | a basic substance | |
| Present | sodium hydrogencarbonate | 0.03 |
| Invention | sodium carbonate | 0.00 |
| | calcium carbonate | 0.00 |
| | magnesium carbonate | 0.00 |
| | magnesium hydroxide | 0.00 |
| | a free radical scavenger | |
| | d-α-tocopherol | 0.00 |
| Control | corn starch | 4.39 |

As shown in [Table 4], the decmposition of Compound A was suppressed by adding a basic substance or a free radical scavenger to the powders comprising Compound A, titanium oxide and polyethylene glycol 6000.

INDUSTRIAL APPLICABILITY

A pharmaceutical preparation of the present invention is stable to light, especially ultraviolet rays or heat, and has excellent storage-stability. Since the surface of a pharmaceutical preparation is uniform, treatments such as sealing, etc., are completed easily and beautifully. Moreover, adhesion of the pharmaceutical preparation to esophagus mucosa on administration is not observed.

A coating agent of the present invention is useful as a material to manufacture a pharmaceutical preparation which has excellent storage-stability as mentioned above. Since the coating agent has superior strength and expandability, it has excellent handling properties and enables uniform coating.

What is claimed is:

1. A stabilized pharmaceutical preparation comprising a tablet coated with a coating agent wherein the coating agent comprises (i) a component for the protection from light present in an amount capable of protecting the pharmaceutical from light, said component being capable of producing free radicals when exposed to ultraviolet rays, and (ii) a free radical scavenger present in an amount capable of scavenging free radicals.

2. The pharmaceutical preparation according to claim 1, wherein the coating agent further comprises an oily substance selected from the group consisting of an ester and an alcohol.

3. The pharmaceutical preparation according to claim 1, wherein the component for the protection from light is a metal oxide.

4. The pharmaceutical preparation according to claim 3, wherein the metal oxide is a titanium oxide, ferric oxide or zinc oxide.

5. The pharmaceutical preparation according to claim 1, wherein the free radical scavenger is sulfites or vitamins.

6. The pharmaceutical preparation according to claim 5, wherein the vitamins are vitamin C or vitamin E.

7. The pharmaceutical preparation according to claim 2, wherein the oily substance is polyethylene glycol.

8. A stabilized pharmaceutical preparation comprising a tablet coated with a coating agent wherein the coating agent comprises (i) titanium oxide present in an amount capable of protecting the pharmaceutical from light and (ii) sodium hydrogensulfite, ascorbic acid, sodium ascorbate, calcium ascorbate, dl-α-tocopherol or dl-α-tocopherol acetate.

9. The pharmaceutical preparation according to claim 2, wherein the coating agent further comprises a basic substance.

10. The pharmaceutical preparation according to claim 9, wherein the basic substance is a metal carbonate or a metal hydroxide.

11. A stabilized pharmaceutical preparation comprising a tablet coated with a coating agent wherein the coating agent comprises (i) an oily substance selected from the group consisting of an ester and an alcohol, and (ii) a free radical scavenger present in an amount capable of scavenging free radicals.

12. A stabilized pharmaceutical preparation comprising a tablet coated with a coating agent wherein the coating agent comprises (i) an oily substance selected from the group consisting of an ester and an alcohol, and (ii) a basic substance.

13. The pharmaceutical preparation according to claim 12, wherein the coating agent further comprises a component for the protection from light, said component being capable of producing free radicals when exposed to ultraviolet rays.

14. A method of stabilizing a pharmaceutical preparation comprising coating a tablet with a coating agent wherein said coating agent comprises (i) a component for the protection from light present in an amount capable of protecting the pharmaceutical from light, said component being capable of producing free radicals when exposed to ultraviolet rays, and (ii) a free radical scavenger present in an amount capable of scavenging free radicals.

15. The method of claim 14, wherein the tablet comprises a composition containing a drug.

16. A method of stabilizing a pharmaceutical preparation comprising coating a tablet with a coating agent wherein said coating agent comprises (i) an oily substance selected from the group consisting of an ester and an alcohol, and (ii) a free radical scavenger present in an amount capable of scavenging free radicals.

17. The method of claim 16, wherein the tablet comprises a composition containing a drug.

18. A method of stabilizing a tablet comprising coating a pharmaceutical preparation with a coating agent wherein said coating agent comprises (i) an oily substance selected from the group consisting of an ester and an alcohol, and (ii) a basic substance.

19. The method of claim 18, wherein the tablet comprises a composition containing a drug.

* * * * *